(12) United States Patent
Lou et al.

(10) Patent No.: US 10,385,041 B2
(45) Date of Patent: Aug. 20, 2019

(54) TERPENE DERIVATIVE-BASED PAR1 INHIBITOR, PREPARATION METHOD THEREOF, AND USE IN TREATMENT OF THROMBOTIC DISEASES

(71) Applicant: SHANDONG UNIVERSITY, Jinan, Shandong (CN)

(72) Inventors: Hongxiang Lou, Jinan (CN); Bin Sun, Jinan (CN); Jun Liu, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 16/068,308

(22) PCT Filed: Jan. 14, 2016

(86) PCT No.: PCT/CN2016/070851
§ 371 (c)(1),
(2) Date: Jul. 5, 2018

(87) PCT Pub. No.: WO2017/107262
PCT Pub. Date: Jun. 29, 2017

(65) Prior Publication Data
US 2019/0023695 A1    Jan. 24, 2019

(30) Foreign Application Priority Data
Dec. 22, 2015 (CN) .......................... 2015 1 0975205

(51) Int. Cl.
| | | |
|---|---|---|
| *C07D 405/04* | (2006.01) | |
| *A61K 31/4427* | (2006.01) | |
| *C07D 213/30* | (2006.01) | |
| *A61P 7/02* | (2006.01) | |

(52) U.S. Cl.
CPC ........ *C07D 405/04* (2013.01); *A61K 31/4427* (2013.01); *A61P 7/02* (2018.01); *C07D 213/30* (2013.01)

(58) Field of Classification Search
CPC .......................... C07D 405/04; A61K 31/4427
See application file for complete search history.

(56) References Cited

U.S. PATENT DOCUMENTS 8,153,664 B2 *    4/2012    Chackalamannil .. C07D 417/06
514/339

FOREIGN PATENT DOCUMENTS

| CN | 101541782 A | 9/2009 |
|---|---|---|
| WO | 2006/041872 A2 | 4/2006 |
| WO | 2006/105217 A2 | 10/2006 |
| WO | 2015/026685 A1 | 2/2015 |
| WO | 2015/026693 A1 | 2/2015 |

OTHER PUBLICATIONS

Sep. 28, 2016 International Search Report issued in International Patent Application No. PCT/CN2016/070851.

* cited by examiner

*Primary Examiner* — Golam M Shameem
(74) *Attorney, Agent, or Firm* — Oliff PLC

(57) ABSTRACT

A novel terpene derivative-based PAR1 inhibitor, a preparation method thereof and a pharmaceutical composition including the same or a salt thereof, as well as a use of the PAR1 inhibitor and the salt thereof in preparation of medicaments for preventing and/or treating thrombotic diseases. The structural formula of the compound is as follows:

The compound has the advantages of clear target, novel structure, low bleeding risk, high safety, outstanding active effect, low preparation cost and the like, and has a great application prospect in the preparation of the medicaments for treating the thrombotic diseases.

9 Claims, No Drawings

TERPENE DERIVATIVE-BASED PAR1 INHIBITOR, PREPARATION METHOD THEREOF, AND USE IN TREATMENT OF THROMBOTIC DISEASES

FIELD OF THE INVENTION

The present invention belongs to the field of blood anti-coagulation technology and specifically relates to a novel terpene derivative-based PAR1 inhibitor, a preparation method thereof and a pharmaceutical composition comprising the same or a salt thereof, as well as a use of the PAR1 inhibitor and the salt thereof in preparation of medicaments for preventing and/or treating thrombotic diseases.

BACKGROUND OF THE INVENTION

In China, with the acceleration of the aging process of the society, the number of patients suffering from cardiovascular diseases has increased rapidly. This type of diseases has long disease courses, high cost, and high mortality rate and disability rate. As the incidence of the cardiovascular diseases caused by vascular embolism has increased year by year, the cardiovascular diseases have become a major public health problem in China.

Studies have shown that platelet overactivation plays an important role in the development and progression of thrombosis and thrombotic diseases. Therefore, inhibiting excessive activation of platelets and reducing adhesion, aggregation and release of the platelets are important means for preventing and treating the thrombotic diseases. At present, anti-platelet medicaments clinically used for preventing and treating the thrombotic diseases are mainly divided into three categories, the first category is the medicaments affecting platelet metabolism enzymes, such as cyclooxygenase inhibitors, thromboxane A2 (TXA2) inhibitors, phosphodiesterase (PDE) inhibitors and the like; the second category is adenosine diphosphate (ADP) inhibitors, such as ticlopidine, clopidogrel, ticagrelor and the like, which inhibit the aggregation of the platelets by inhibiting $P2Y_{12}$ receptors of the platelets; and the third category is platelet GP $II_b/III_a$ receptor antagonists, such as abciximab and eptifibatide, which inhibit the aggregation of the platelets by competitively blocking binding of fibrinogen with GP $II_b/III_a$ receptors on the surfaces of the platelets. Most of the above traditional anti-platelet medicaments resist thrombosis by inhibiting TXA2 or ADP. However, because both TXA2 and ADP participate in the normal hemostasis process and play an important role in the process, TXA2 or ADP inhibitors also affect the normal hemostatic function of a human body while blocking the pathological thrombosis process, thereby increasing the probability and risk of bleeding in the patient.

Protease-activated receptor-1 (PAR) is a member of a G-protein coupled receptor family. Humans have four receptor subtypes, namely PAR1, PAR2, PAR3 and PAR4. However, only PAR1 and PAR4 are distributed on the surfaces of the platelets. PAR1 plays a more important role in the thrombin-mediated platelet activation process. Thrombin can activate PAR1 at a relatively low concentration and further activate the platelets, resulting in rapid aggregation of the platelets. Inhibition of the PAR1 receptor can block the thrombin-mediated platelet aggregation and pathological thrombus expansion process without affecting the normal protective hemostasis process of the human body, in which TXA2 and ADP participate. Thus, PAR1 is an ideal anti-platelet medicament target.

Vorapaxar Sulfate is a PAR1 inhibitor which is first created by Merck Sharp & Dohme Ltd, and was approved by FDA for marketing in May 2014. The medicament is used for the patients suffering from heart attacks or the patients with blocked arteries in legs, and can further reduce the risk of the heart attacks and strokes. As the Vorapaxar blocks the platelet aggregation by inhibiting PAR1, the medicament does not affect the normal hemostasis process and can reduce the risk of accidental bleeding in the patient. Although the Vorapaxar has good anti-coagulation activity, it has the disadvantages of a complicated structure (having 7 chiral centers), a long synthetic route (16 linear synthesis steps) and high preparation cost.

Natural products are important sources for research and development of novel medicaments due to the characteristics of various kinds, complicated structure, clear chirality, fixed conformation and the like. The cheap and readily available natural products are used as starting raw materials or precursors of the medicaments to perform structural transformation and modification, so that rapid construction and large-scale preparation of the medicaments can be achieved, and the production cost can be also effectively reduced. Andrographolide, which is a diterpenoid compound, and polygodial, which is a sesquiterpenoid compound, are common important active natural products, and their structural formulas are as follows:

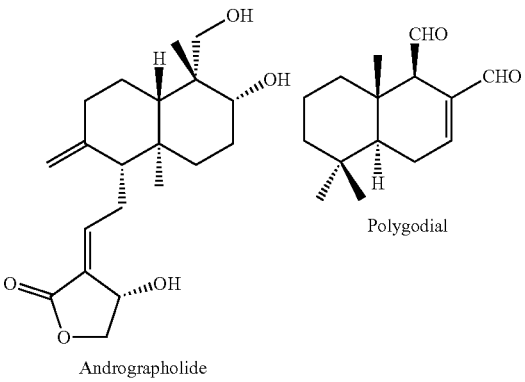

Andrographolide

Polygodial

The conformation of the chiral center in each structure is identical to the corresponding conformation of the key chiral center in the structure of Vorapaxar. Therefore, under the premise of ensuring that the conformation of the key chiral center remains unchanged, using the diterpenoid compound and the sesquiterpenoid compound as the precursors to perform structural modification and transformation is an important way to rapidly discover novel PAR1 inhibitor type medicaments.

SUMMARY OF THE INVENTION

In view of the above deficiencies of the prior art, the present invention aims at providing an anti-platelet and anti-thrombotic disease medicament, and the medicament has the advantages of clear and novel target, low bleeding risk, high safety, outstanding active effect, low preparation cost and the like, and can be used as a very promising medicament for treating the thrombotic diseases.

To achieve the foregoing objective, the present invention adopts the following technical solution:

A compound as shown in formula (I) or a pharmaceutically acceptable salt thereof,

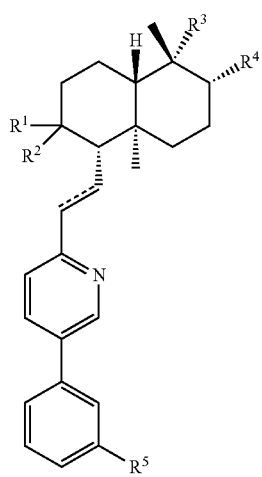

(I)

wherein === represents a single bond or a double bond; $R^1$ and $R^2$ respectively represent a hydrogen atom, a halogen atom, a hydroxyl group, a ($C_1$-$C_4$) alkyl group, a ($C_1$-$C_4$) alkoxyl group or a ($C_1$-$C_4$) hydroxyalkyl group;

or $R^1$ and $R^2$ co-form a double bond;

or $R^1$ and $R^2$ co-form a spiro ring or a heterospiro ring having 3-7 atoms;

$R^3$ and $R^4$ respectively represent a hydrogen atom, a hydroxyl group, a ($C_1$-$C_4$) alkyl group, a ($C_1$-$C_4$) hydroxyalkyl group or a ($C_1$-$C_4$) alkoxyl group;

or $R^3$ represents —C(O)$R^6$, —C(O) O$R^6$, —CO(O)$R^6$, —COSO$R^6$, or —C(O) N$R^6R^7$; or $R^4$ represents —O(O)C$R^8$, —OSO$R^8$, —OSO$_2R^8$, —NHC(O)O$R^8$, —NHC(O)$R^8$, —NHCONH$R^8$, —NHC(O)N$R^8R^9$, or —NHSO$_2R^8$;

or $R^4$ represents an oxygen atom, and forms a double bond, namely a ketone carbonyl group with a carbon atom connected therewith;

$R^5$ represents a halogen atom, a trifluoromethoxyl group or a trifluoromethyl group;

$R^6$, $R^7$, $R^8$ and $R^9$ are independently selected from a hydrogen atom, a ($C_1$-$C^6$) alkyl group, an ester group, a carboxylic acid group, a phenyl group and a benzyl group.

Preferably, $R^1$ and $R^2$ respectively represent a hydrogen atom or a ($C_1$-$C_4$) hydroxyalkyl group, or $R^1$ and $R^2$ co-form a heterospiro ring having 3-7 atoms; $R^3$ represents a ($C_1$-$C_4$) hydroxyalkyl group, a methoxymethyl group, a formyl group, a formyl methyl ester group, an aldehyde group or a formamide group; $R^4$ is a hydroxyl group, a methoxyl group or a ketone carbonyl group; and $R^5$ is a halogen atom or a trifluoromethyl group.

Further preferably, the heterospiro ring co-formed by $R^1$ and $R^2$ is a three-membered oxygen ring.

An example of the above compound is as follows:

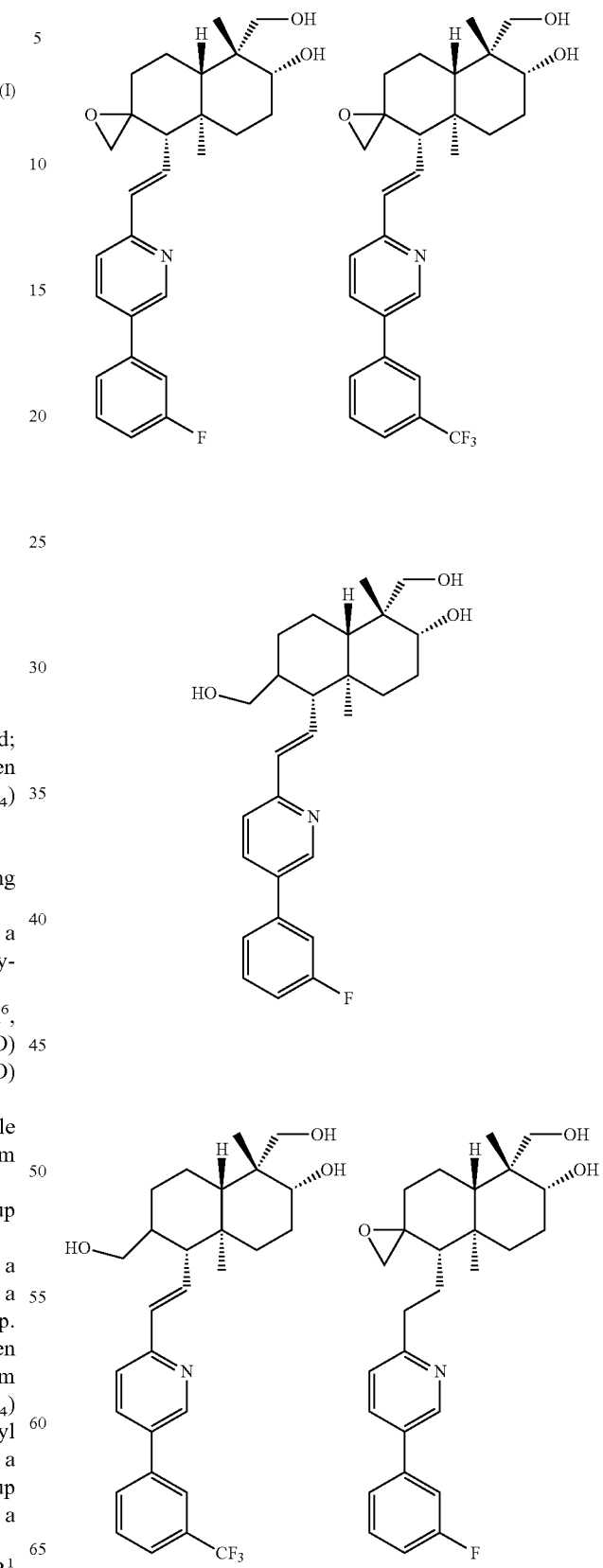

-continued
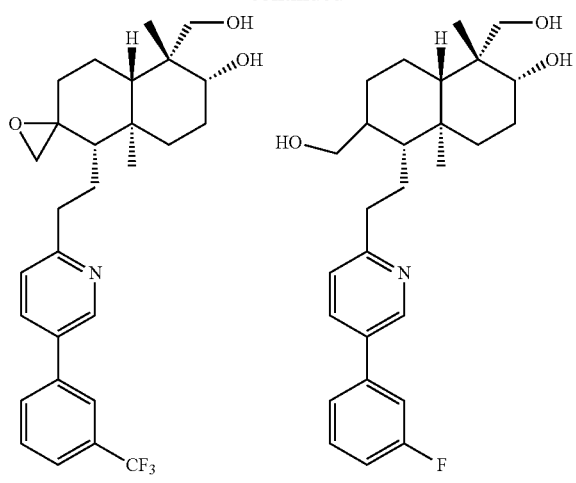
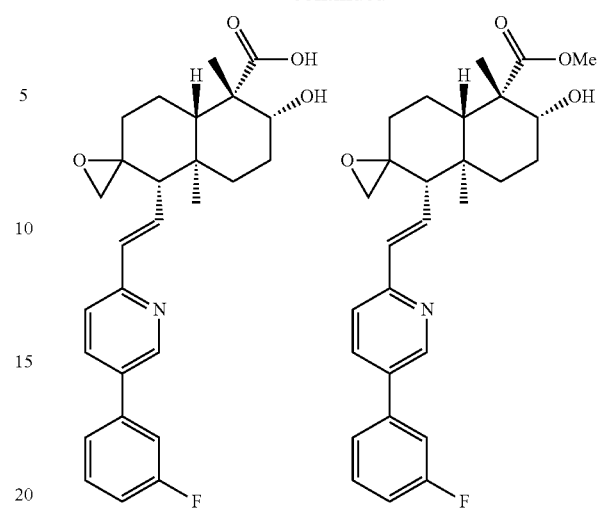
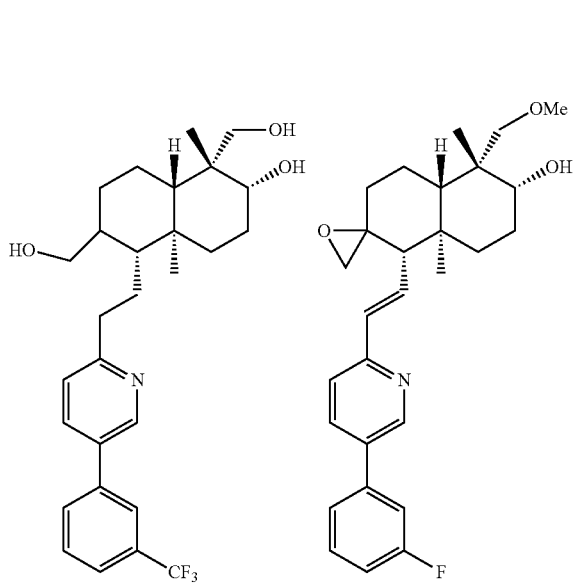
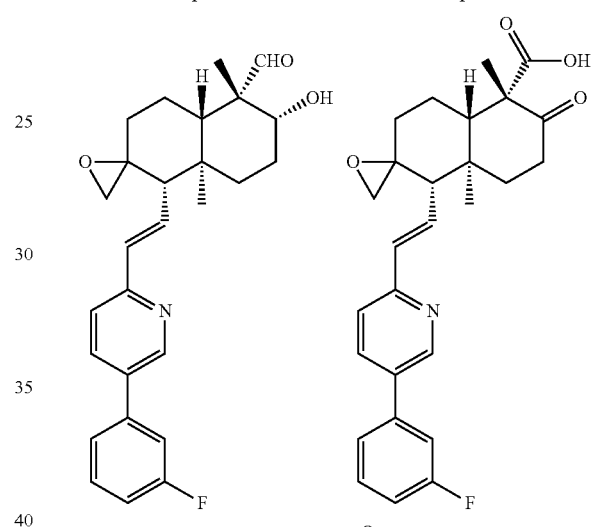
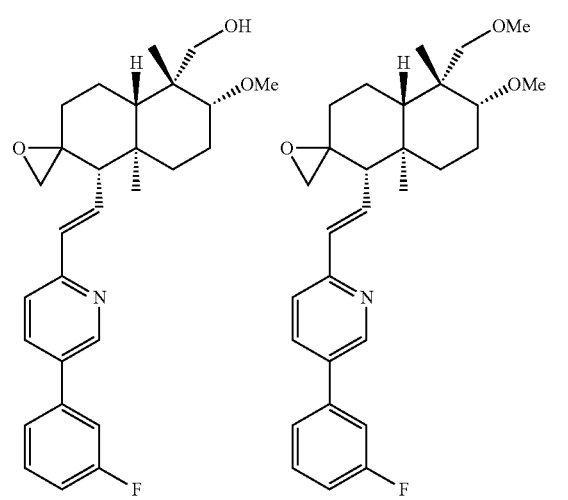
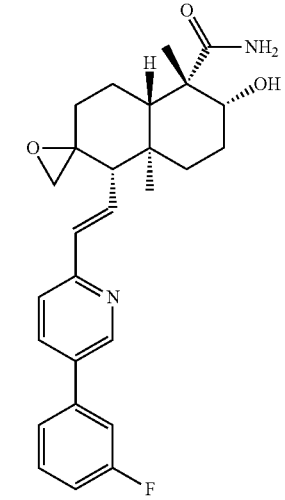
Preferably, the pharmaceutically acceptable salt of the above compound is a salt formed by the above compound and an inorganic acid, such as hydrochloric acid, sulfuric acid, nitric acid or hydrobromic acid; or a salt of formed by the above compound and an organic acid, such as methanesulfonic acid, toluenesulfonic acid or trifluoroacetic acid.

Unless otherwise indicated, the term "($C_1$-$C_4$) alkoxyl group" represents a group —O—R, wherein R is a ($C_1$-$C_4$) alkyl group.

The term "($C_1$-$C_4$) hydroxyalkyl group" represents a ($C_1$-$C_4$) alkyl group substituted by a hydroxyl group.

The term "spiro ring" represents that $R_1$ and $R_2$ are connected through a covalent bond and co-form a cyclic structure with spiro atoms on a six-membered carbocyclic ring.

The term "heterospiro ring" represents that in the spiro ring constituted by $R_1$, $R_2$ and the spiro atoms, one or more hetero atoms, such as oxygen atoms, nitrogen atoms, sulfur atoms or the like are included.

The present invention additionally provides a method for preparing the compound of formula (I), and the compound can be obtained as detailed below.

The preparation method of the above compound comprises: enabling the compound as shown in formula (II) to react with the compound as shown in formula (III) to obtain the compound as shown in formula (I).

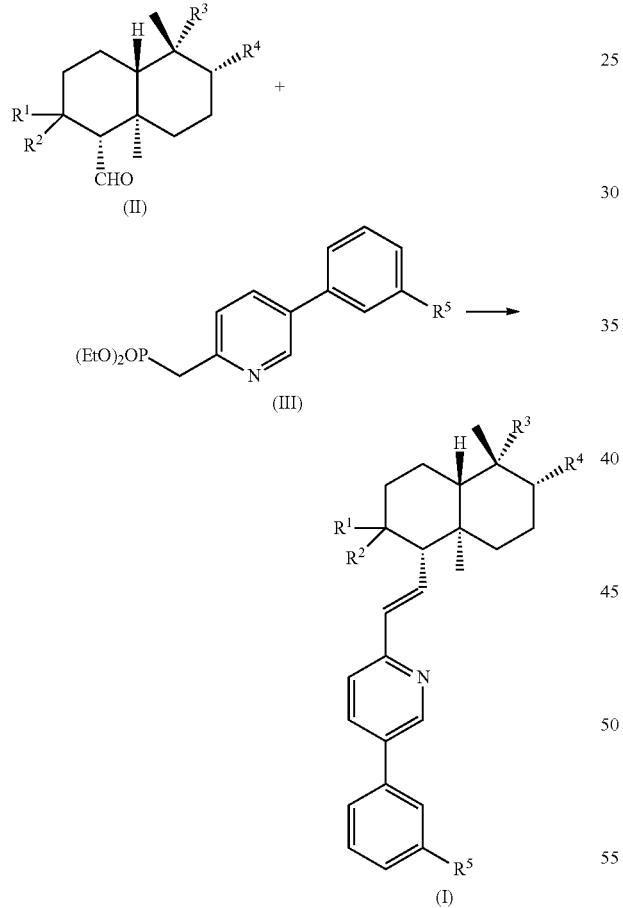

$R^1$, $R^2$, $R^3$, $R^4$ and $R^5$ are as defined before. In addition, $R^3$ and $R^4$ can also represent a co-formed 4 to 8-membered carbocyclic or heterocyclic ring.

The preparation method of the compound as shown in formula (II) is as follows: using andrographolide as a starting raw material to perform dehydrating rearrangement reaction with aluminium oxide to prepare the compound as shown in formula (IV), enabling the compound of formula (IV) to perform epoxidation reaction with m-CPBA, further performing acetalization reaction with 2, 2-dimethoxypropane, and finally reacting with ozone to prepare the compound as shown in formula (II).

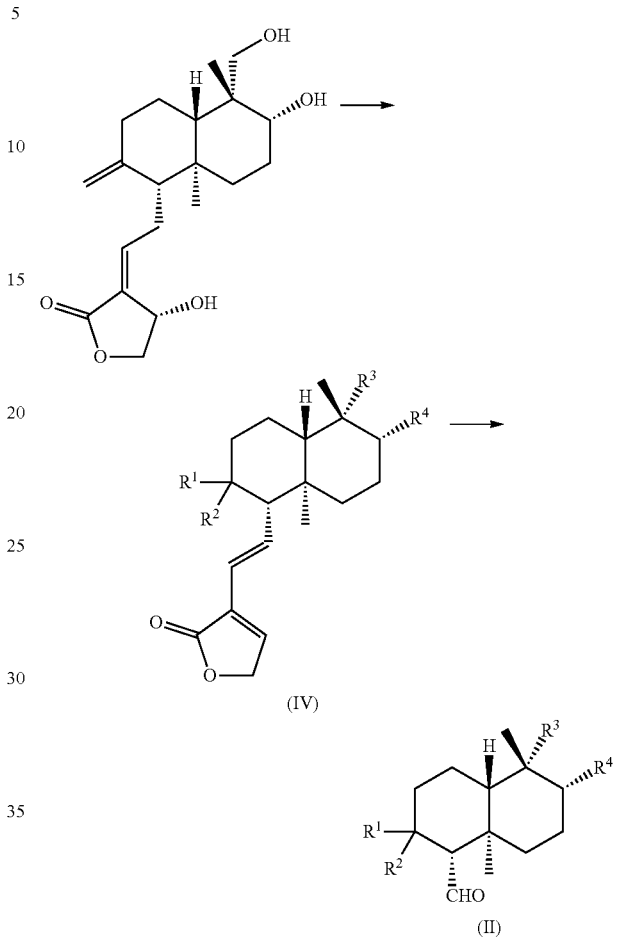

andrographolide $R^1$, $R^2$, $R^3$, $R^4$ and $R^5$ are as defined before. In addition, $R^3$ and $R^4$ can also represent a co-formed 4 to 8-membered carbocyclic or heterocyclic ring.

The present invention also provides a use of the above compound or the pharmaceutically acceptable salt thereof in preparation of medicaments for preventing and/or treating thrombotic diseases, such as the use in preparation of a PAR1 inhibitor. The thrombotic diseases include thrombosis, atherosclerosis, restenosis, hypertension, angina pectoris, heart failure, myocardial infarction, glomerulitis, peripheral vascular diseases and the like.

The present invention further provides a pharmaceutical composition, containing the above compound or the pharmaceutically acceptable salt thereof.

Preferably, the pharmaceutical composition further contains one or more pharmaceutically acceptable carriers, excipients and/or diluents.

Preferably, the pharmaceutical composition contains one or more pharmaceutically or bromatologically acceptable excipients. The adopted excipients can be solid or liquid. The preparations in solid form include powder, tablets, dispersible granules, capsules, pills and suppositories. The powder and the tablets can contain about 5% to about 95% of active ingredients. The appropriate solid excipients can be magnesium carbonate, magnesium stearate, talcum powder, sugar or lactose. The tablets, the powder, the pills and the capsules are solid dosage forms which are suitable for oral administration. The preparations in liquid form include solution, suspension and emulsion, and the embodiments thereof are water solution or water-propylene glycol solution for parenteral injection, or oral solution added with a sweetener and a contrast agent. In addition, the pharmaceutical composition can also be prepared into vial injections for injection, freeze-dried powder for injection, large infusion solution or small infusion solution.

Preferably, the pharmaceutical composition is a solid oral preparation, a liquid oral preparation or an injection.

Further preferably, the pharmaceutical composition is tablets, dispersible tablets, enteric-coated tablets, chewable tablets, orally disintegrating tablets, capsules, sugar-coated tablets, granules, dry powder, oral solution, vial injections for injection, freeze-dried powder for injection, large infusion solution or small infusion solution. We have found that the compound as shown in formula (I) and the pharmaceutically acceptable salt thereof prepared according to the present invention are medicaments which can be used for preventing and/or treating thrombosis, atherosclerosis, restenosis, hypertension, angina pectoris, heart failure, myocardial infarction, glomerulitis or peripheral vascular diseases.

Thus, another subject of the present invention is a method for treating a mammal suffering from thrombosis, atherosclerosis, restenosis, hypertension, angina pectoris, heart failure, myocardial infarction, glomerulitis or peripheral vascular diseases, and the method comprises applying a therapeutically effective amount of the above compound of formula (I).

The term "therapeutically effective amount" used therein represents the amount of a therapeutic agent required for treating and improving the targeted disease or symptoms or exhibiting a detectable therapeutic effect.

The compound of the present invention is effective in a quite wide dosage range. The dosage at which the compound as shown in formula (I) of the present invention is administered can be decided by a doctor according to relevant circumstances. These circumstances include the physical condition of the subject, the route of administration, age, body weight, individual response to the medicament, severity of the symptoms and the like.

In the treatment process, the compound of formula (I) or the pharmaceutically acceptable salt thereof can also be used in combination with at least one of other cardiovascular disease medicaments. The atomic compositions or structures of the covered other cardiovascular disease medicaments are different from that of the compound of formula (I). The other cardiovascular disease medicaments which can be used in combination with the novel compound of the present invention include medicaments with anti-thrombosis, anti-platelet aggregation, anti-atherosclerosis, anti-restenosis and/or anti-coagulation activity, and these medicaments can be used for treating thrombosis-related diseases, including thrombosis, atherosclerosis, restenosis, hypertension, angina pectoris, arrhythmia, heart failure, myocardial infarction, glomerulitis, thrombotic stroke, thromboembolic stroke, peripheral vascular diseases, other cardiovascular diseases and other diseases in which thrombin and receptors thereof have pathological effects.

The present invention has the following beneficial effects:

(1) The compound of the present invention has the advantages of clear target, novel structure, low bleeding risk, high safety, outstanding active effect, low preparation cost and the like, and has a great application prospect in the preparation of the medicaments for treating the thrombotic diseases.

(2) The starting raw material for preparing the compound of the present invention is andrographolide or polygodial. Andrographolide is a common active natural product, which is cheap and easy to obtain. Andrographolide is used as the raw material, and under the premise of ensuring that the conformation of the key chiral center is unchanged, through 6 to 7 steps of structural modification and transformation, a variety of compounds with brand new structures can be rapidly prepared and obtained on a large scale, and good economy is also achieved.

DETAILED DESCRIPTION OF THE EMBODIMENTS

The present invention will be further described in combination of embodiments. It should be noted that the following description is only used for explaining the present invention, rather than limiting the content of the present invention.

Embodiment 1: Preparation of Compounds I-1 and I-2

(1) Step 1: Preparation of Compound 1

Andrographolide (500 mg) was weighed and placed in a round-bottom flask, pyridine was added thereto to dissolve it, and aluminum oxide (200 mg) was added into the solution, followed by heating and stirring. After the end of the reaction, the system was cooled to room temperature, the aluminum oxide was removed by filtration, the solvent was evaporated under reduced pressure, and the purification was performed by column chromatography (DCM/MeOH) to obtain the white solid compound 1.

MS m/z 333 (M+1); $^1$H NMR (400 MHz, DMSO) δ 7.65 (s, 1H), 6.74 (dd, J=15.8, 10.1 Hz, 1H), 6.12 (d, J=15.8 Hz, 1H), 5.05 (d, J=4.9 Hz, 1H), 4.89 (s, 2H), 4.73 (s, 1H), 4.42 (s, 1H), 4.14 (dd, J=7.4, 2.7 Hz, 1H), 3.84 (dd, J=10.9, 2.6 Hz, 1H), 3.31-3.14 (m, 2H), 2.36 (d, J=10.5 Hz, 2H), 1.98 (dd, J=14.1, 7.5 Hz, 1H), 1.72 (d, J=13.0 Hz, 1H), 1.65-1.50 (m, 2H), 1.46-1.25 (m, 2H), 1.23-1.11 (m, 2H), 1.09 (s, 3H) 0.76 (s 3H).

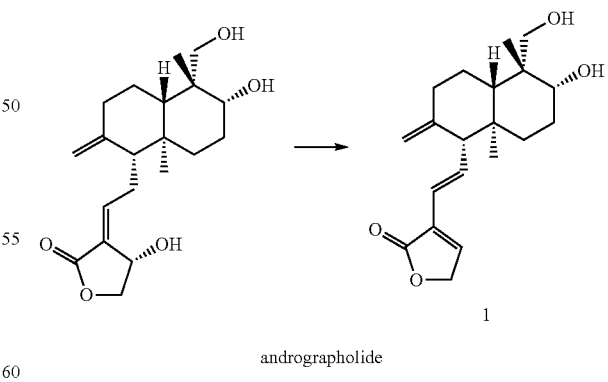

andrographolide (2) Step 2: Preparation of Compound 2

The pure compound 1 (0.3 mmol) and K$_2$CO$_3$ (0.5 mmol) were placed in a round-bottom flask, dichloromethane was added, the system was cooled to 0° C., m-CPBA was slowly added, and the system was heated to room temperature after the end of adding. After the end of the reaction, pure water and the dichloromethane were added for extraction, then washing with saline solution, drying with magnesium sulfate and filtering were performed, the solvent was evaporated under reduced pressure, and the purification was performed by column chromatography to obtain the white solid compound 2.

MS m/z 349 (M+1); $^1$H NMR (400 MHz, Acetone) δ 7.48 (s, 1H), 6.49 (dd, J=15.5, 9.9 Hz, 1H), 6.15 (d, J=15.6 Hz, 1H), 4.84 (s, 2H), 4.53 (s, 1H), 4.15 (d, J=10.8 Hz, 1H), 3.69 (s, 1H), 3.38 (dd, J=34.6, 15.0 Hz, 3H), 2.85 (s, 1H), 2.72 (d, J=3.5 Hz, 1H), 2.51 (d, J=4.5 Hz, 1H), 2.20 (d, J=9.8 Hz, 1H), 1.93-1.52 (m, 6H), 1.43 (dd, J=26.2, 13.5 Hz, 2H), 1.23 (s, 4H), 0.99 (s, 3H).

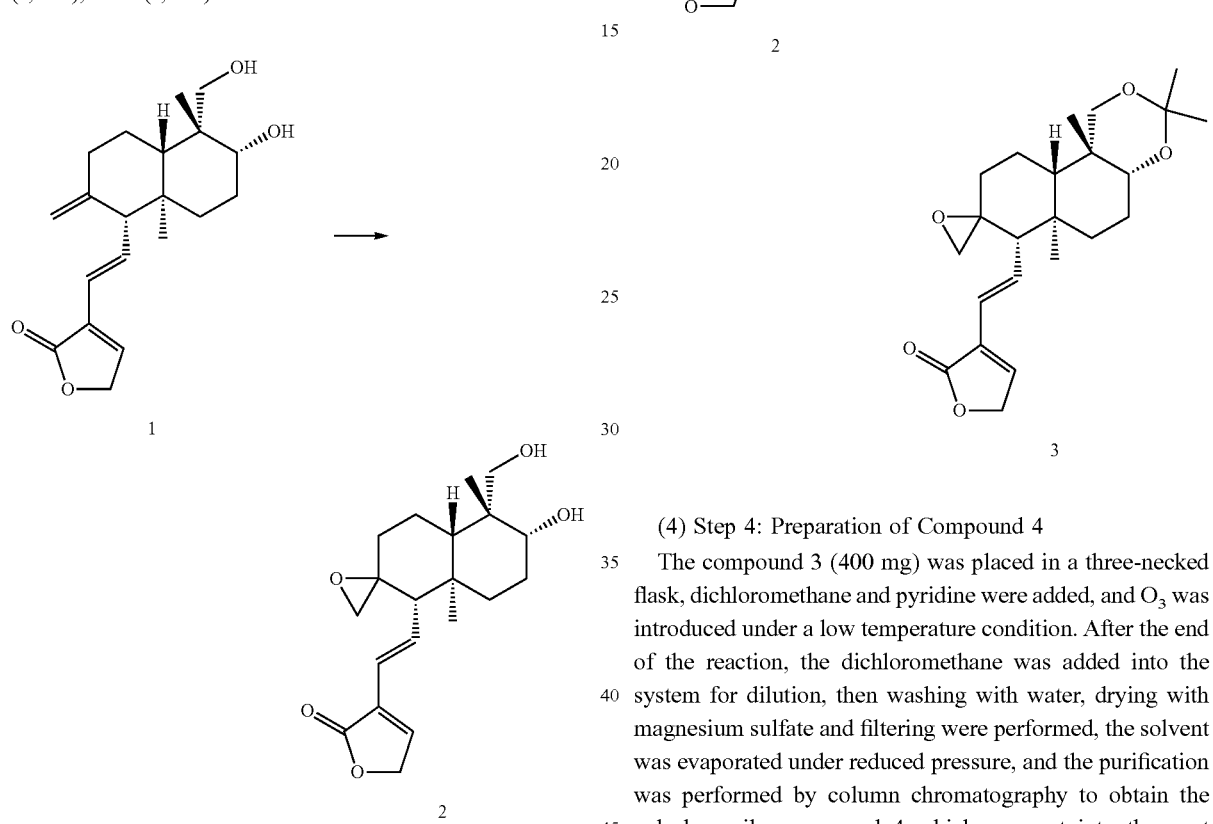

(3) Step 3: Preparation of Compound 3

The compound 2 (6.91 g) was weighed and placed in a round-bottom flask, dichloromethane was added thereto to dissolve it, and 2, 2-dimethoxypropane (25 mL) and pyridinium p-toluenesulfonate (PPTS, 800 mg) were successively added. After the end of the reaction, water was added, the water layer was extracted with the dichloromethane, organic layers were merged, then drying with magnesium sulfate and filtering were performed, the solvent was evaporated under reduced pressure, and the purification was performed by column chromatography to obtain the white solid compound 3.

MS m/z 389 (M+1); $^1$H NMR (400 MHz, Acetone) δ 7.49 (s, 1H), 6.54 (dd, J=15.6, 9.9 Hz, 1H), 6.17 (d, J=15.7 Hz, 1H), 4.85 (d, J=1.4 Hz, 2H), 4.06 (d, J=11.6 Hz, 1H), 3.45 (dd, J=9.6, 4.3 Hz, 1H), 3.23 (d, J=11.6 Hz, 1H), 2.73 (dd, J=4.7, 1.6 Hz, 1H), 2.53 (d, J=4.7 Hz, 1H), 2.26 (d, J=9.9 Hz, 1H), 2.09-1.96 (m, 2H), 1.92-1.76 (m, 2H), 1.71 (s, 1H), 1.57 (dd, J=12.9, 4.0 Hz, 1H), 1.53-1.41 (m, 2H), 1.40-1.34 (m, 4H), 1.28 (s, 4H), 1.27-1.16 (m, 8H).

(4) Step 4: Preparation of Compound 4

The compound 3 (400 mg) was placed in a three-necked flask, dichloromethane and pyridine were added, and O$_3$ was introduced under a low temperature condition. After the end of the reaction, the dichloromethane was added into the system for dilution, then washing with water, drying with magnesium sulfate and filtering were performed, the solvent was evaporated under reduced pressure, and the purification was performed by column chromatography to obtain the colorless oily compound 4 which was put into the next reaction after purification.

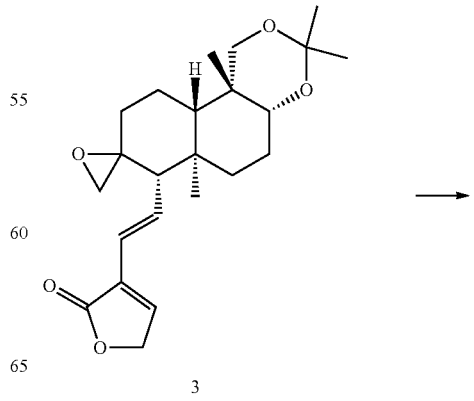

-continued

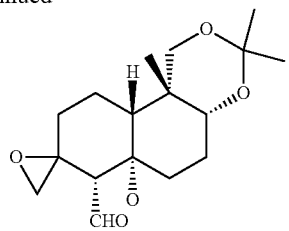

4

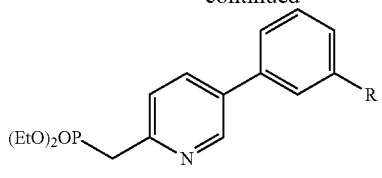

5 R = F
6 R = CF₃

(5) Step 5: Preparation of Compound 7 or 8

The compound 5 or 6 (0.5 mmol) was placed in a flask, tetrahydrofuran was added thereto to dissolve it, a hexane solution of n-butyllithium (2.5 M/L) was added dropwise under a low temperature condition, after the end of adding, the system was heated to room temperature and stirred continuously, then a tetrahydrofura solution of the compound 4 (0.4 mmol) was added, stirring was performed till the end of the reaction, then a saturated ammonium chloride solution was added dropwise for quenching reaction, ethyl acetate was added, the organic layer was washed with water, drying with magnesium sulfate and filtering were performed, the solvent was evaporated under reduced pressure, and the purification was performed by column chromatography to obtain the white solid compound 7 or 8.

Compound 7: MS m/z 478 (M+1); ¹H NMR (400 MHz, CDCl3), δ: 8.75 (d, J=2 Hz, 1H), 7.79 (d, J=8 Hz, 1H), 7.44 (m, 1H), 7.35 (d, 8 Hz, 1H), 7.24 (m, 2H), 7.08 (m, 1H), 6.54 (d, J=3.2 Hz, 2H), 4.11 (d, J=11.6 Hz, 1H), 3.51 (dd, J=6 Hz, 4 Hz, 1H), 3.30 (d, J=11.6 Hz, 1H), 2.92 (d, J=4 Hz, 1H), 2.61 (d, J=4.4 Hz, 1H), 2.41 (t, J=4.4 Hz, 1H), 1.96 (m, 2H), 1.84 (m, 1H), 1.76 (m, 1H), 1.62 (m, 1H), 1.52 (m, 2H), 1.44 (s, 3H), 1.38 (s, 3H), 1.29 (s, 3H), 1.25 (s, 3H), 1.21 (m, 3H).

Compound 8: MS m/z 527 (M+1); ¹H NMR (400 MHz, CDCl3) δ 8.69 (s, 1H), 7.70 (dd, J=26.0, 8.2 Hz, 3H), 7.54 (dd, J=18.4, 7.6 Hz, 2H), 7.18 (d, J=8.5 Hz, 1H), 6.47 (s, 2H), 4.02 (d, J=11.5 Hz, 1H), 3.43 (dd, J=9.8, 3.8 Hz, 1H), 3.22 (d, J=11.7 Hz, 1H), 2.84 (d, J=3.4 Hz, 1H), 2.53 (d, J=4.0 Hz, 1H), 2.34 (d, J=5.6 Hz, 1H), 2.05-1.84 (m, 2H), 1.78 (d, J=13.9 Hz, 1H), 1.68 (dd, J=13.4, 5.2 Hz, 1H), 1.58 (dd, J=13.5, 4.9 Hz, 1H), 1.45 (t, J=11.8 Hz, 2H), 1.37 (s, 3H), 1.30 (d, J=8.1 Hz, 4H), 1.20 (d, J=15.1 Hz, 8H).

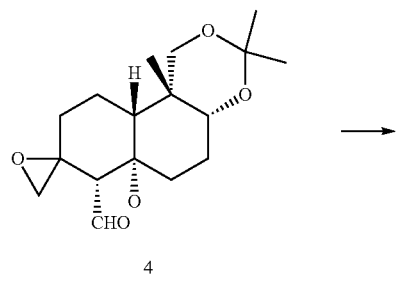

4

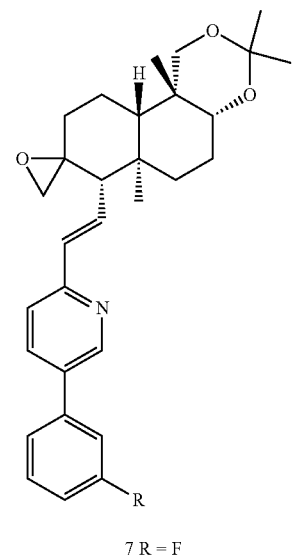

7 R = F
8 R = CF₃

(6) Step 6: Preparation of Compound I-1 or I-2

The pure compound 7 or 8 (500 mg) was weighed and placed in a round-bottom flask, methanol was added thereto to dissolve it, Amberlyst-15 (100 mg) was added, and then stirring was performed. After the end of the reaction, filtering was performed, the solvent was evaporated, and the purification was performed by column chromatography to obtain the white product compound I-1 or I-2.

I-1: MS m/z 438 (M+1); ¹H NMR (400 MHz, CDCl3), δ: 8.74 (s, 1H), 7.82 (d, J=8 Hz, 1H), 7.46 (q, J=7.6 Hz, 1H), 7.35 (d, J=7.6 Hz, 1H), 7.25 (2H), 7.11 (t, J=8.4 Hz, 1H), 6.52 (m, 1H), 6.52 (m, 1H), 4.27 (d, J=10.8 Hz, 1H), 3.53 (d, J=9.2 Hz, 1H), 3.40 (m, 1H), 3.21 (m, 2H), 2.92 (d, 3.6 Hz, 1H), 2.61 (d, 4 Hz, 1H), 2.38 (d, 7.6 Hz, 1H), 1.96 (m, 2H), 1.81 (m, 1H), 1.74 (m, 1H), 1.62 (m, 1H), 1.52 (m, 2H), 1.30 (s, 3H), 1.19 (m, 2H), 1.04 (s, 3H).

I-2: MS m/z 488 (M+1); ¹H NMR (400 MHz, CDCl3) δ 8.76 (d, J=1.9 Hz, 1H), 7.87-7.78 (m, 2H), 7.75 (d, J=7.6 Hz, 1H), 7.63 (dt, J=15.4, 7.7 Hz, 2H), 7.30-7.26 (m, 1H), 6.50 (dt, J=15.3, 12.2 Hz, 2H), 5.31 (s, OH), 4.27 (d, J=10.7 Hz, 1H), 3.59-3.47 (m, 1H), 3.45-3.27 (m, 3H), 2.92 (d, J=3.6 Hz, 1H), 2.62 (d, J=4.3 Hz, 1H), 2.39 (d, J=9.1 Hz, 1H), 1.95 (d, J=11.2 Hz, 2H), 1.88-1.79 (m, 1H), 1.78-1.69 (m, 1H), 1.69-1.60 (m, 1H), 1.53 (dd, J=18.2, 7.1 Hz, 2H), 1.32 (s, 3H), 1.27-1.23 (m, 1H), 1.21 (s, 1H), 1.05 (s, 3H).

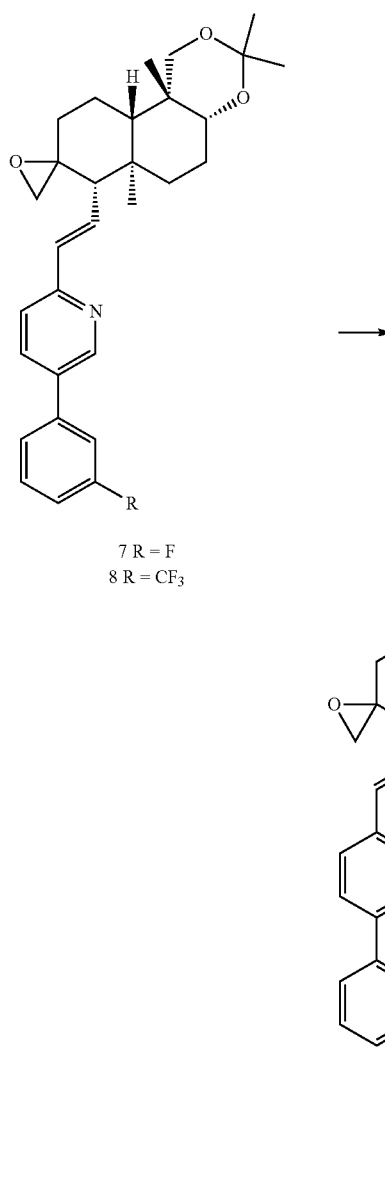

7 R = F
8 R = CF₃

I-1 R = F
I-2 R = CF₃

Embodiment 2: Preparation of Compounds I-3 and I-4

85 mg of titanocene dichloride and 40 mg of zinc powder were placed into a tetrahydrofuran solution, and the tetrahydrofuran solution of the compound I-1 or I-2 (60 mg) and 1,4-cyclohexadiene (80 μL) was added into the reaction system dropwise. After the end of the reaction, a saturated water solution of sodium dihydrogen phosphate was added, stirring was performed till the end of the reaction, then filtering was performed, ethyl acetate was added, washing was performed with water three times, drying with sodium sulfate and filtering were performed, the solvent was evaporated, and the separation and the purification were performed by silica gel column chromatography to obtain the compound I-3 and I-4.

I-3: MS m/z 442 (M+1); $^1$H NMR (400 MHz, CDCl$_3$), δ: 8.68 (s, 1H), 7.84 (dd, J=6 Hz, 2 Hz, 1H), 7.45 (dd, J=8 Hz, 6 Hz, 1H), 7.34 (d, J=7.6 Hz, 1H), 7.29 (1H), 7.25 (1H), 7.08 (t, J=8.4 Hz, 1H), 4.10 (d, J=11.2 Hz, 1H), 3.74 (m, 3H), 3.58 (d, J=12 Hz, 1H), 3.48 (dd, J=6.4 Hz, 4 Hz, 1H), 3.14 (m, 2H), 2.59 (m, 1H), 2.27 (m, 1H), 1.84 (m, 3H), 1.65 (m, 2H), 1.49 (m, 2H), 1.18 (s, 3H), 0.92 (s, 3H), 0.79 (m, 2H).

I-4: MS m/z 492 (M+1); $^1$H NMR (400 MHz, CDCl3), δ: 8.72 (s, 1H), 7.88 (d, J=8 Hz, 1H), 7.79 (s, 1H), 7.75 (d, J=7.6 Hz, 1H), 7.67 (d, J=7.6 Hz, 1H), 7.62 (d, J=7.6 Hz, 1H), 7.33 (d, J=8 Hz, 1H), 4.10 (m, 2H), 3.78 (d, J=12 Hz, 1H), 3.59 (d, J=12 Hz, 1H), 3.51 (dd, J=10.8 Hz, 4.8 Hz, 1H), 3.15 (d, J=12.4 Hz, 2H), 2.92 (br, 2H), 2.64 (t, J=12.8 Hz, 1H), 2.28 (m, 1H), 2.04 (s, 1H), 1.91 (m, 2H), 1.66 (m, 3H), 1.53 (m, 3H), 1.25 (s, 3H), 1.19 (s, 3H).

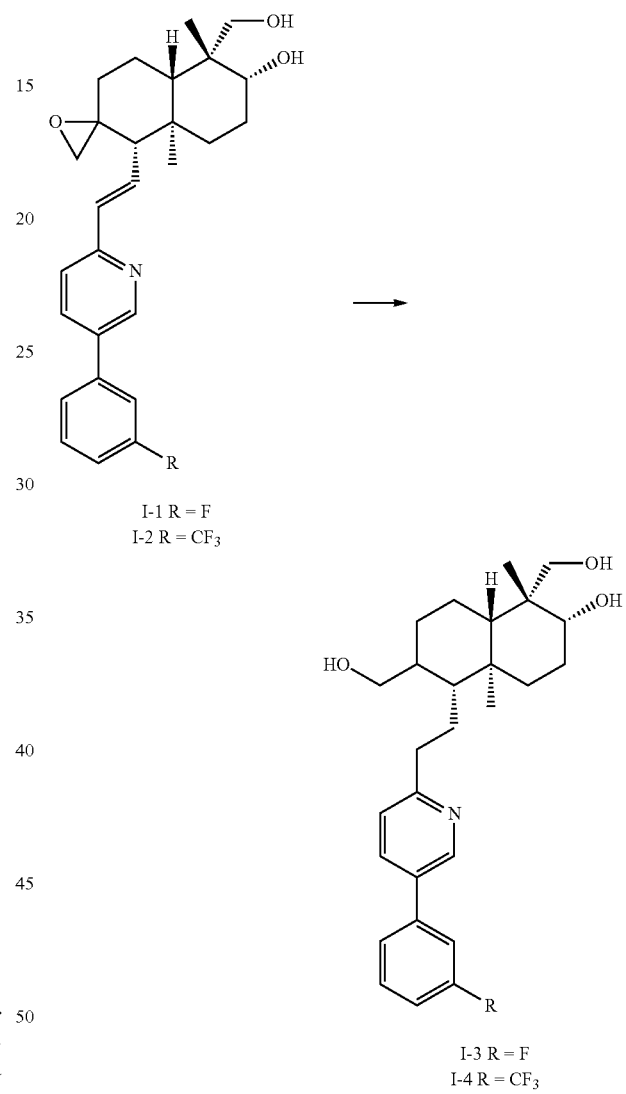

I-1 R = F
I-2 R = CF₃

I-3 R = F
I-4 R = CF₃

Embodiment 3: Preparation of Compounds I-5 and I-6

The compound I-1 (0.1 mmol) was dissolved in THF (2 mL), NaH (0.2 mmol) was added, stirring was performed, and CH$_3$I (0.25 mmol) was added dropwise, followed by stirring until the end of the reaction. Ethyl acetate and water were added for extraction, washing was performed with water, drying was performed with anhydrous Na$_2$SO$_4$, then filtering was performed, the solvent was evaporated under reduced pressure, and the purification was performed by column chromatography to obtain I-5 and I-6.

I-5: MS m/z 452 (M+1); $^1$H NMR (400 MHz, CDCl$_3$), δ: 8.75 (d, J=1.6 Hz, 1H), 7.82 (d, J=7.2 Hz, 1H), 7.44 (m, 1H), 7.35 (d, J=8 Hz, 1H), 7.24 (m, 2H), 7.09 (td, J=8.4 Hz, 2 Hz, 1H), 6.54 (m, 2H), 3.93 (d, J=9.2 Hz, 1H), 3.87 (d, J=7.2 Hz, 1H), 3.33 (s, 3H), 3.28 (d, J=9.2 Hz, 1H), 2.94 (d, J=3.6 Hz, 1H), 2.60 (d, J=4.4 Hz, 1H), 2.39 (d, J=9.2 Hz, 1H), 1.95 (s, 1H), 1.92 (t, J=2 Hz, 1H), 1.78 (m, 1H), 1.70 (m, 1H), 1.65 (m, 2H), 1.56 (dd, J=12.8 Hz, 4 Hz, 1H), 1.51 (m, 1H), 1.27 (s, 3H), 1.21 (m, 2H), 1.07 (s, 3H).

I-6: MS m/z 452 (M+1); $^1$H NMR (400 MHz, CDCl$_3$), δ: 8.75 (s, 1H), 7.83 (d, J=7.2 Hz, 1H), 7.44 (dd, J=14.4 Hz, 8 Hz, 1H), 7.35 (d, J=7.6 Hz, 1H), 7.27 (m, 2H), 7.11 (m, 1H), 6.54 (m, 2H), 4.17 (d, J=8.8 Hz, 1H), 3.37 (s, 3H), 3.26 (m, 2H), 3.00 (dd, J=12 Hz, 4.4 Hz, 1H), 2.92 (d, J=3.6 Hz, 1H), 2.61 (d, J=4.4 Hz, 1H), 2.37 (d, J=8.4 Hz, 1H), 1.94 (m, 2H), 1.70 (m, 2H), 1.60 (m, 2H), 1.52 (m, 1H), 1.25 (s, 3H), 1.21 (m, 2H), 1.03 (s, 3H).

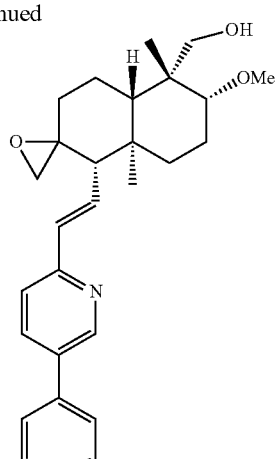

I-6

Embodiment 4: Preparation of Compounds I-7, I-8 and I-9

(1) Preparation of Compound I-7

The compound I-1 (0.5 mmol) was dissolved in dichloromethane, TEMPO, a K$_2$CO$_3$—NaHCO$_3$ buffer solution, TBAI (0.05 mmol) and NCS were added under a low temperature condition, stirring was performed at room temperature till the end of the reaction, ethyl acetate was added, washing was performed with distilled water, drying was performed with anhydrous Na$_2$SO$_4$, filtering was performed, the solvent was evaporated under reduced pressure, the purification was performed by column chromatography to obtain the white solid I-7.

I-7: MS m/z 436 (M+1); $^1$H NMR (400 MHz, CDCl3), δ: 10.01 (s, 1H), 8.85 (d, J=2 Hz, 1H), 8.07 (dd, J=8 Hz, 2.4 Hz, 1H), 7.62 (m, 4H), 7.24 (td, J=8 Hz, 1.6 Hz, 1H), 6.48 (m, 2H), 5.16 (br, 1H), 2.80 (d, J=4.4 Hz, 1H), 2.54 (d, J=4.8 Hz, 1H), 2.44 (d, J=8.8 Hz, 1H), 1.97 (m, 4H), 1.51 (d, J=13.2 Hz, 1H), 1.37 (m, 4H), 1.12 (s, 3H), 0.86 (s, 3H).

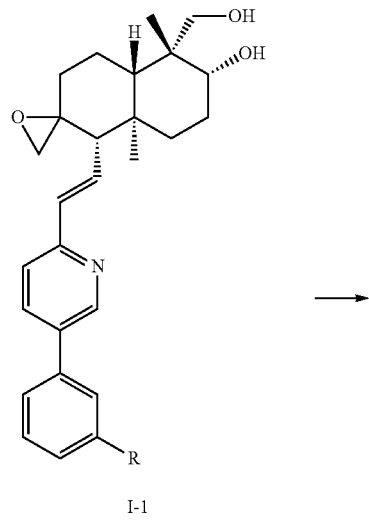

I-1

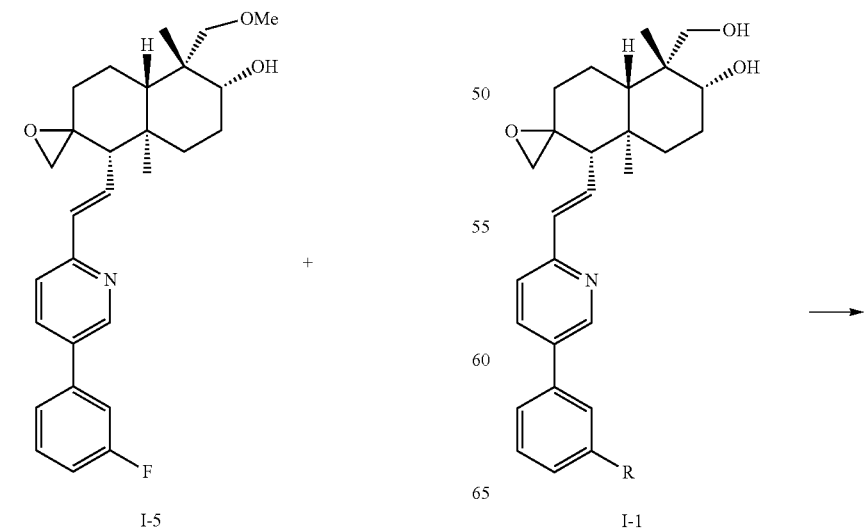

I-5 + I-1

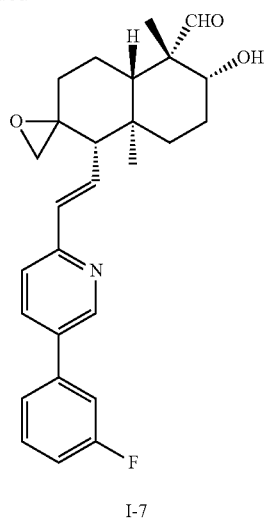

I-7

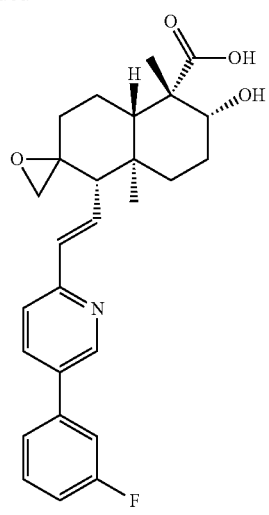

I-8

(2) Preparation of Compound I-8

The compound I-7 (0.4 mmol) was dissolved in a mixed solvent of isopentane, tert-butanol and THF, a NaClO$_2$—NaH$_2$PO$_4$ buffer solution was added dropwise under an ice bath condition, and stirring was performed at room temperature till the end of the reaction. Ethyl acetate was added, washing was performed with distilled water, and the purification was performed by column chromatography to obtain the white solid I-8.

I-8: MS m/z 452 (M+1); $^1$H NMR (400 MHz, CDCl$_3$), δ: 12.41 (br, 1H), 8.84 (d, J=2 Hz, 1H), 8.08 (dd, J=8 Hz, 2 Hz, 1H), 7.59 (m, 4H), 7.23 (td, J=8.4 Hz, 1.6 Hz, 1H), 6.48 (m, 2H), 4.40 (br, 1H), 3.12 (dd, J=12 Hz, 4 Hz, 1H), 2.81 (d, J=4 Hz, 1H), 2.57 (d, J=4.4 Hz, 1H), 2.36 (d, J=7.6 Hz, 1H), 2.07 (m, 1H), 1.94 (m, 1H), 1.84 (m, 1H), 1.56 (m, 1H), 1.46 (m, 1H), 1.39 (m, 1H), 1.31 (s, 3H), 1.26 (m, 2H), 0.94 (s, 3H).

(3) Preparation of Compound I-9

The compound I-8 (0.5 mmol) was dissolved in DMF, then K$_2$CO$_3$ (1.25 mmol) was added, and CH$_3$I (2.5 mmol) was slowly added dropwise, and the reaction system was stirred until the end of the reaction. Ethyl acetate was added, washing was performed with distilled water, drying was performed with anhydrous Na$_2$SO$_4$, and the purification was performed by column chromatography to obtain the compound I-9.

I-9: MS m/z 466 (M+1); $^1$H NMR (400 MHz, CDCl$_3$), δ: 8.75 (s, 1H), 7.81 (d, J=4 Hz, 1H), 7.43 (q, J=4.8, 1H), 7.34 (d, J=5.2 Hz, 1H), 7.24 (2H), 7.08 (t, J=5.2 Hz, 1H), 6.53 (br, 2H), 3.71 (s, 3H), 3.25 (d, J=8 Hz, 1H), 3.16 (td, J=8 Hz, 2.4 Hz, 1H), 2.93 (s, 1H), 2.63 (d, J=2.8 Hz, 1H), 2.39 (d, J=5.2 Hz, 1H), 2.10 (m, 1H), 2.04 (m, 1H), 1.95 (m, 2H), 1.81 (m, 1H), 1.71 (d, J=9.2 Hz, 1H), 1.52 (d, J=7.2 Hz, 1H), 1.46 (s, 3H), 1.25 (m, 2H), 0.92 (s, 3H).

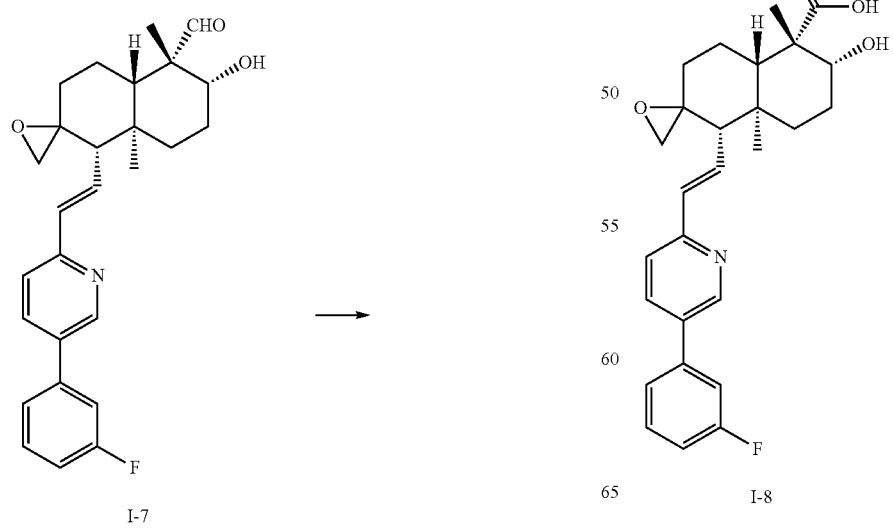

I-7 → I-8 →

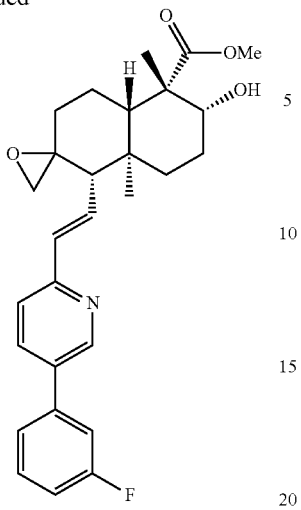

I-9

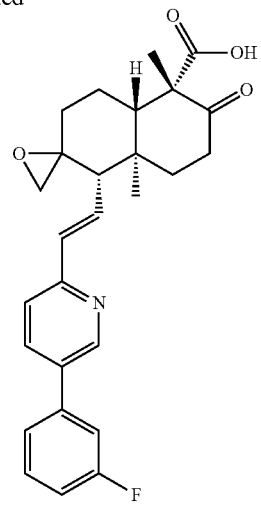

I-10

Embodiment 5: Preparation of Compounds I-10

The compound I-1 (0.05 mmol) was dissolved in anhydrous DCM, PCC (0.15 mmol) was added into the reaction system, stirring was performed till the end of the reaction, filtering was performed, ethyl acetate was added into filtrate, washing was performed with distilled water, drying was performed with $Na_2SO_4$, and the solvent was evaporated under reduced pressure to obtain the white solid. Then, DCM was added thereto to dissolve it, TEMPO, a K2CO3-NaHCO3 buffer solution, TBAI (0.05 mmol) and NCS were successively added, and stirring was performed till the end of the reaction. Ethyl acetate was added for dilution, washing was performed with distilled water, drying was performed with $Na_2SO_4$, filtering was performed, the solvent was evaporated under reduced pressure, and the purification was performed by column chromatography to obtain the compound I-10.

I-10: MS m/z 450 (M+1); $^1$H NMR (400 MHz, $CDCl_3$), δ: 8.84 (d, J=2 Hz, 1H), 8.08 (m, 1H), 7.61 (m, 4H), 7.25 (m, 1H), 6.50 (m, 2H), 2.94 (dd, J=14.8 Hz, 6 Hz, 1H), 2.87 (d, J=4 Hz, 1H), 2.62 (d, J=4.4 Hz, 1H), 2.22 (m, 2H), 1.90 (m, 2H), 1.75 (m, 1H), 1.61 (d, J=10.8 Hz, 1H), 1.49 (m, 2H), 1.41 (m, 2H), 1.27 (s, 3H), 1.22 (s, 3H).

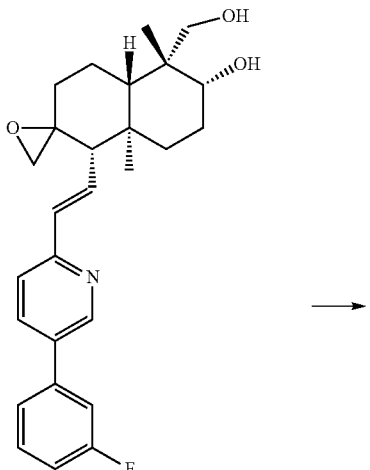

I-1

Embodiment 6: Determination of Biological Activity (PAR1 Inhibition Activity) of the Compound 1. Cell Culture 1.1 Cell Resuscitation An HEK293-Ga15-PAR1 cell strain (HD Biosciences stable cell strain) was quickly taken out of a liquid nitrogen tank, and shaken continuously in a 37° C. water bath until it was completely melted. A cell suspension was quickly added into a pre-heated culture medium (90% DMEM+10% FBS+ 1× Pen/Strep), placed in a centrifuge and centrifuged at 1000 rpm for 10 minutes. A centrifugal tube was taken out, the supernatant was discarded, and the fresh pre-heated culture medium was added into the centrifugal tube, cells were resuspended, and the cell suspension was added into a culture dish and cultured at 37° C. with 5% of $CO_2$.

1.2 Passage

When the cells reached 80-90% of the culture dish, the cells were gently washed with 0.05% of trypsin-EDTA, part of digestive juice was removed, then the cells were incubated for 2-3 min, the digestion was terminated with the new culture medium, the cells were gently blew with a gun head, and the cells were resuspended. In general, the passage was performed according to 1:4 to 1:8 every 2 to 3 days.

2. Calcium Ion Influx Experiment 2.1 Cell Plate Coating

On the day before the experiment, 1× Matrigel (Brand: BD, Cat #: 356230) was added into a clean 384-well cell plate, incubated at 37° C. for 30 minutes, and then inverted and centrifuged at 500 rpm for 30 seconds to remove the coating solution.

2.2 Plating

The cell precipitate was digested and collected, resuspended in the culture medium to $3\times10^5$ cells/mL, added into the coated cell plate according to 50 μL per well and then incubated at 37° C. with 5% of $CO_2$ overnight.

2.3 Preparation of Buffer Solution

On the day of the experiment, the fresh experimental buffer solution and 0.5× Calcium 4 (Brand: Molecular Devices, Cat #: R8141) loading buffer solution were prepared.

2.4 Preparation of Compound

The 30 mM DMSO stock solution was first diluted with DMSO to 10 mM, and then diluted 4 times from 10 mM for a total of 10 concentrations. Ten DMSO concentration gradients of the compound were added into the experimental buffer solution at a ratio of 1:20 to prepare a working solution of the compound (5 times the final reaction concentration). After that, the working solution of the compound was transferred into a 384-well compound plate according to the layout in the following drawing for later use.

Positive control: 40 mM DMSO stock solution of the reference compound SCH79797 was diluted to 2 mM;

Negative control: 5% of DMSO prepared from the experimental buffer solution 2.5 Preparation of PAR1 Agonist haTRAP 10 mM DMSO stock of the agonist haTRAP was diluted with the experimental buffer solution to 18 µM (6 times the final reaction concentration 3 µM), and then transferred into a 384-well compound plate, at least at 25 µl/well for later use.

2.6 Dye Incubation

The cell plate incubated overnight was taken out, the cell culture medium was removed by centrifugation at 300 rpm for 30 seconds, 20 µL of freshly prepared 0.5× Calcium 4 loading buffer solution was added into every well and then incubation was performed at 37° C. with 5% of $CO_2$ for 1 hour.

2.7 Adding of Compound

The compound working solution was transferred from the compound plate to the cell plate at 5 µL/well according to the layout, then placed at 37° C. again and incubated with 5% of $CO_2$ for 15 minutes.

2.8 Adding of Agonist and Reading of Fluorescent Signals

The agonist was transferred from the 384-well compound plate (FLIPR) to the cell plate at 5 µL/well according to the program set by FLIPR, and the fluorescent signals in each well of the cell plate were simultaneously read.

3. Data Analysis

The inhibition rate (%) of the compound in each well on the cell plate was calculated according to the fluorescence signal values of the positive control and the negative control on each cell plate. The positive control contains a high concentration of the reference compound (400 µM of SCH79797) and is 100% inhibition control; and the negative control does not contain any compound, only has the DMSO (1% of DMSO) as the solvent of the compound and is 0% inhibition control. The inhibition rates and the corresponding concentrations of the compounds obtained by calculation were introduced into the relevant software for graphing, and the $IC_{50}$ values of the compounds were calculated according to the 4-PL dosage-effect formula. The $IC_{50}$ result of the reference compound is also one of standards for testing the quality of every experiment.

The activity screening results of part of the compounds are as shown in Table 1.

The activity screening results show that the compounds I-1 to I-10 have significant in-vitro anti-PAR1 activity, and the $IC_{50}$ values are in the range of 0.66-19 µM. The in-vitro PAR1 inhibition activity of each of the compounds I-7 and I-9 is obviously improved in comparison with the positive control medicament SCH79797, and the $IC_{50}$ values are 3.52 µM and 0.66 µM respectively.

The invention claimed is:

1. A compound as shown in formula (I) or a pharmaceutically acceptable salt thereof,

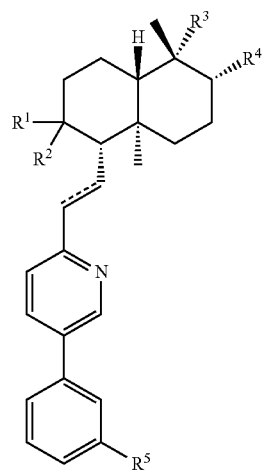

(I)

wherein === represents a single bond or a double bond;
$R^1$ and $R^2$ respectively represent a hydrogen atom, a halogen atom, a hydroxyl group, a ($C_1$-$C_4$) alkyl group, a ($C_1$-$C_4$) alkoxyl group or a ($C_1$-$C_4$) hydroxyalkyl group;
or $R^1$ and $R^2$ co-form a double bond;
or $R^1$ and $R^2$ co-form a spiro ring or a heterospiro ring having 3-7 atoms;
$R^3$ and $R^4$ respectively represent a hydrogen atom, a hydroxyl group, a ($C_1$-$C_4$) alkyl group, a ($C_1$-$C_4$) hydroxyalkyl group or a ($C_1$-$C_4$) alkoxyl group;
or $R^3$ represents —C(O)$R^6$, —C(O) O$R^6$, —CO(O)$R^6$, —COS$R^6$ or —C(O)NR$^6$R$^7$;
or $R^4$ represents —O(O)CR$^8$, —OSO$R^8$, —OSO$_2$R$^8$, —NHC(O)OR$^8$, —NHC(O)R$^8$, —NHCONHR$^8$, —NHC(O)NR$^8$R$^9$ or —NHSO$_2$R$^8$;
or $R^4$ represents an oxygen atom, and forms a double bond, namely a ketone carbonyl group with a carbon atom connected therewith;
$R^5$ represents a halogen atom, a trifluoromethoxyl group or a trifluoromethyl group;
$R^6$, $R^7$, $R^8$ and $R^9$ are independently selected from a hydrogen atom, a ($C_1$-$C^6$) alkyl group, an ester group, a carboxylic acid group, a phenyl group and a benzyl group.

TABLE 1

| Dosage effect results of part of compounds | | | | | | | | | | | |
|---|---|---|---|---|---|---|---|---|---|---|---|
| | SCH79797 | I-1 | I-2 | I-3 | I-4 | I-5 | I-6 | I-7 | I-8 | I-9 | I-10 |
| Slope | 0.95 | 2.87 | 4.62 | 2.09 | 5.00 | 2.59 | 1.53 | 1.02 | 1.97 | 0.97 | 1.23 |
| $IC_{50}$ (µM) | 8.71 | 7.76 | 7.95 | 8.91 | 8.76 | 7.07 | 10.96 | 3.52 | 31.64 | 0.66 | 19.71 |

2. The compound or the pharmaceutically acceptable salt thereof according to claim 1, wherein $R^1$ and $R^2$ respectively represent a hydrogen atom or a $(C_1-C_4)$ hydroxyalkyl group, or $R^1$ and $R^2$ co-form a heterospiro ring having 3-7 atoms; $R^3$ represents a $(C_1-C_4)$ hydroxyalkyl group, a methoxymethyl group, a formyl group, a formyl methyl ester group, an aldehyde group or a formamide group; $R^4$ is a hydroxyl group, a methoxyl group or a ketone carbonyl group; and $R^5$ is a halogen atom or a trifluoromethyl group.

3. The compound or the pharmaceutically acceptable salt thereof according to claim 2, wherein the heterospiro ring which is co-formed by $R^1$ and $R^2$ is a three-membered oxygen ring.

4. The compound or the pharmaceutically acceptable salt thereof according to claim 1, wherein the compound is selected from the structures:

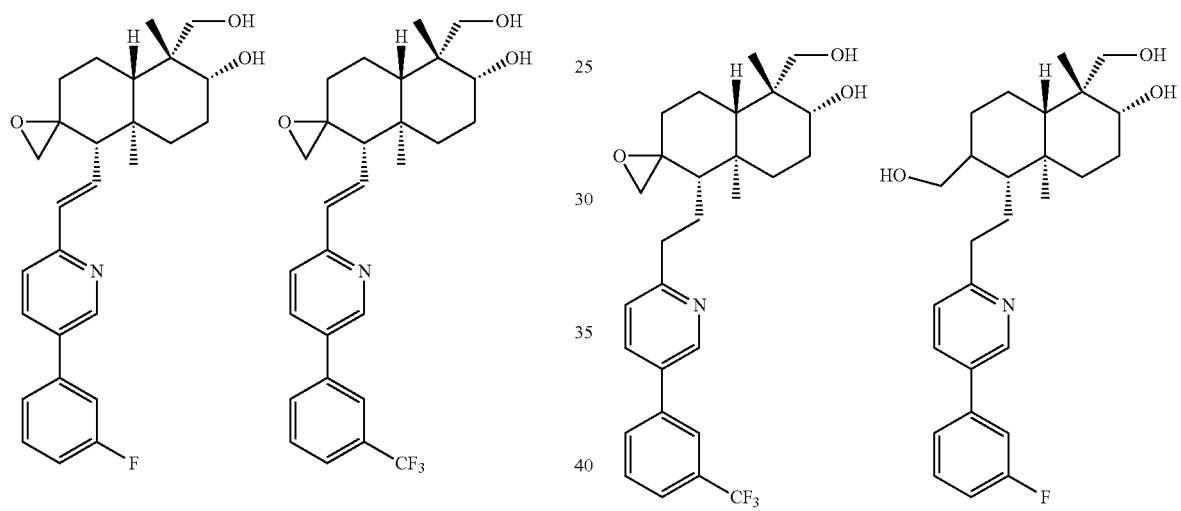

-continued

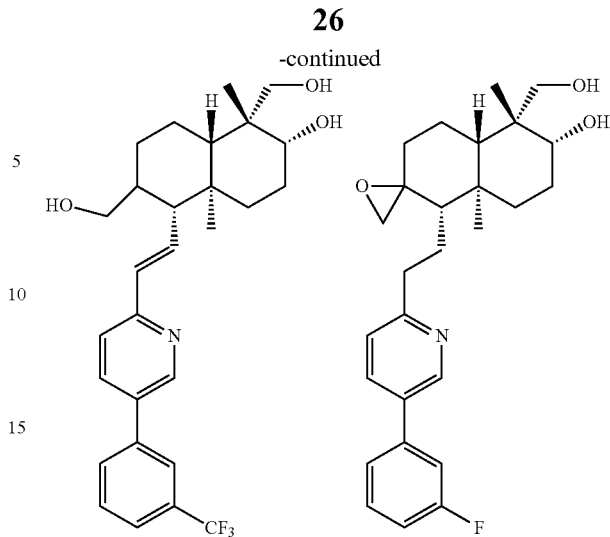

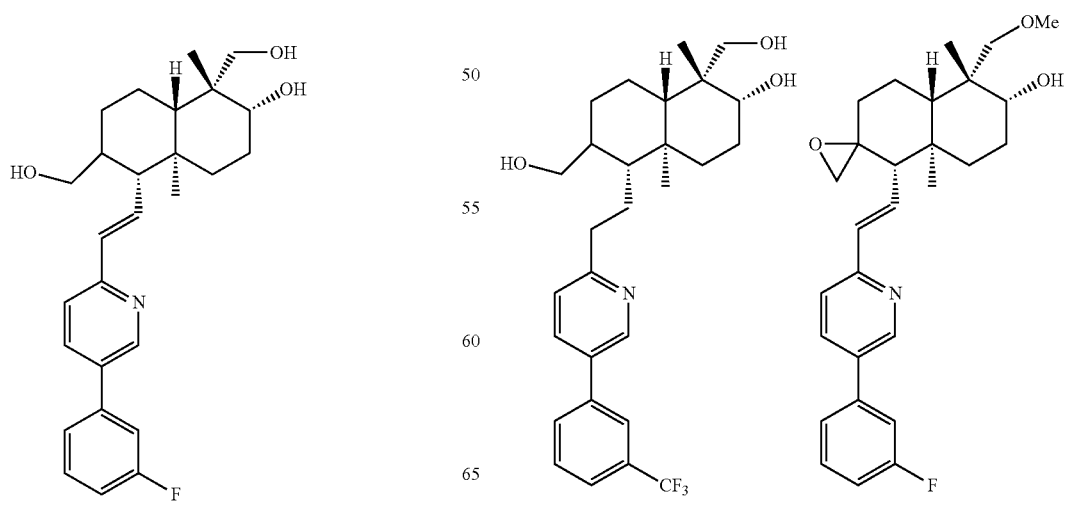

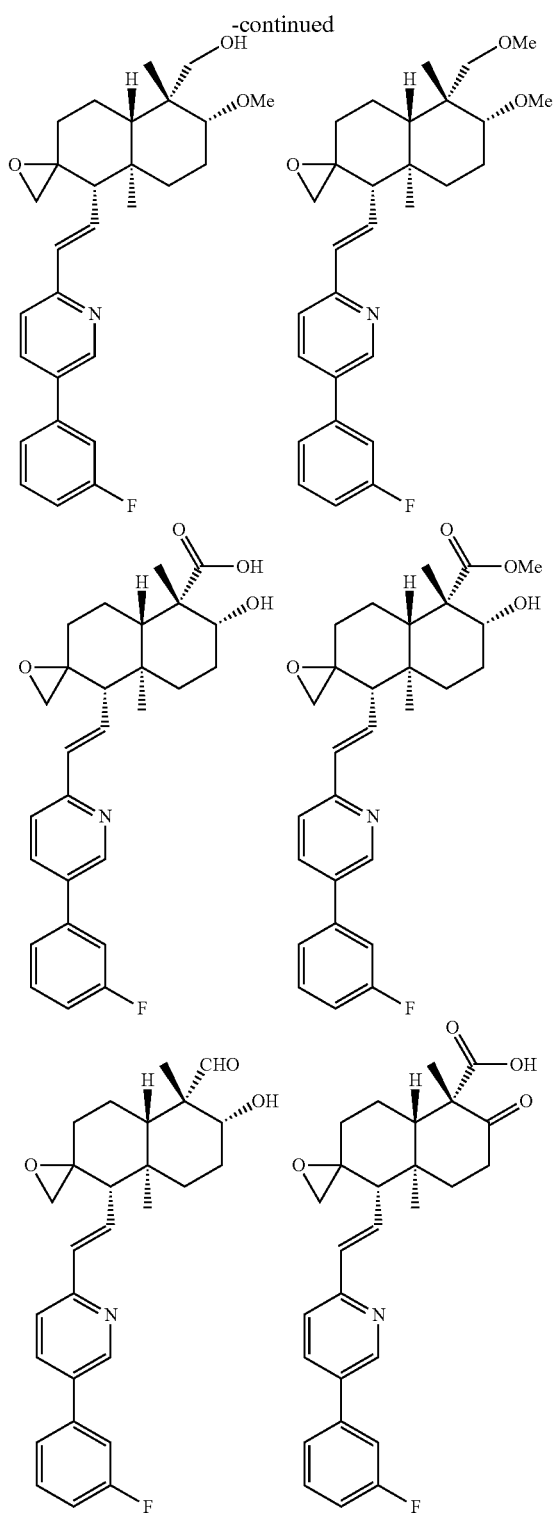

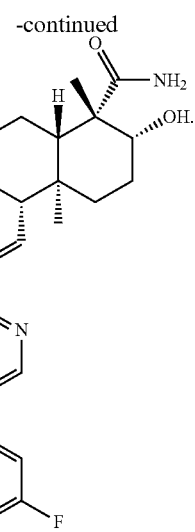

5. The compound or the pharmaceutically acceptable salt thereof according to claim 1, wherein the pharmaceutically acceptable salt of the compound is a salt formed by the compound and an inorganic acid or an organic acid.

6. A pharmaceutical composition, containing the compound or the pharmaceutically acceptable salt thereof according to claim 1.

7. The pharmaceutical composition according to claim 6, wherein the pharmaceutical composition further comprises one or more pharmaceutically acceptable carriers, excipients and/or diluents.

8. The pharmaceutical composition according to claim 6, wherein the pharmaceutical composition is a solid oral preparation, a liquid oral preparation or an injection.

9. The pharmaceutical composition according to claim 8, wherein the pharmaceutical composition is tablets, dispersible tablets, enteric-coated tablets, chewable tablets, orally disintegrating tablets, capsules, sugar-coated tablets, granules, dry powder, oral solution, vial injections for injection, freeze-dried powder for injection, large infusion solution or small infusion solution.

* * * * *